United States Patent [19]
Chirikjian et al.

[11] Patent Number: 5,656,430
[45] Date of Patent: Aug. 12, 1997

[54] OSCILLATING SIGNAL AMPLIFIER FOR NUCLEIC ACID DETECTION

[75] Inventors: Jack G. Chirikjian, Potomac; G. Bruce Collier, Gaithersburg, both of Md.

[73] Assignee: Trevigen, Inc., Gaithersburg, Md.

[21] Appl. No.: 483,089

[22] Filed: Jun. 7, 1995

[51] Int. Cl.[6] ................................................ C12Q 1/68
[52] U.S. Cl. ............................................................ 435/6
[58] Field of Search ............................................. 435/6

[56] References Cited

U.S. PATENT DOCUMENTS

| | | | |
|---|---|---|---|
| 4,876,187 | 10/1989 | Duck et al. | 1/68 |
| 5,011,769 | 4/1991 | Duck et al. | 1/68 |

FOREIGN PATENT DOCUMENTS

| | | |
|---|---|---|
| WO9320233 | 10/1993 | WIPO. |
| WO95/07361 | 3/1995 | WIPO. |
| WO95/12688 | 5/1995 | WIPO. |
| WO95/14106 | 5/1995 | WIPO. |

OTHER PUBLICATIONS

Lu et al. "Detection of Single DNA Base Mutations with Mismatch Repair Enzymes," *Genomics*, 14, No. 2 pp. 249–255 (1992).

Hsu et al. "Detection of DNA Point Mutations with DNA Mismatch Repair Enzymes," *Carcinogenesis*, vol. 15, No. 8. pp. 1657–1662 (1994).

Yao et al. "Strand-specific Cleavage of Mismatch-containing DNA by Deoxyinosine 3'-Endonuclease from *Escherichia coli*," Journal of Biological Chemistry, vol. 269, No. 50, pp. 31390–31396 (1994).

Au et al. "*Escherichia coli mutY* gene product is required for specific A-G→C•G Mismatch Correction," *Proc. Natl. Acad. Sci. USA*, vol. 85, pp. 9163–9166 (1988).

Tsai–Wu et al. "*Escherichia coli* MutY protein has both N–glycosylase and apurinic/apyrimidinic endonuclease activities on A-C and A-G mispairs," *Proc. Natl. Acad. USA*, vol. 89, pp. 8779–8783, (1992).

Youil et al. "Screening for mutations by enzyme mismatch cleavage with T4 endonuclease VII", *Pro. Natl. Acad. Sci. USA*, vol. 92, pp.87–91 (1995).

Corey et al. "Sequence–Selective Hydrolysis of Duplex DNA by an Oligonucleotide–Directed Nuclease," *J. Am. Chem. Soc.* 1989, vol. 111, pp. 8523–8525 (1989).

Nölling et al. "Modular Organization of Related Archaeal plasmids encoding different restriction—modification systems in *Methanobacterium thermoformicicum*, *Nucleic Acids Research*," vol. 20, No. 24, pp. 6501–6507 (1992).

Duck et al. "Probe Amplifier System Based on Chimeric Cycling Oligonucleotides", *Bio Techniques*, 9(2): 142–147, (1990).

*Primary Examiner*—Stephanie W. Zitomer
*Assistant Examiner*—Ethan Whisenant
*Attorney, Agent, or Firm*—Foley & Lardner

[57] ABSTRACT

The present invention provides several methods employing nucleic acid repair enzymes. The present invention provides a method for detecting point mutations in nucleic acid sequences. The present invention further provides a method for detecting non-mutated or wild-type nucleic acid sequences. The present invention also enhances target polynucleotide detection using an oscillation reaction and tail labeling techniques. The present invention also provides helix destabilizing molecule and similar molecules to enhance the hybridization of the probe to the target polynucleotides. Finally, this invention provides a method for determining the repair index for a mismatched or damaged oligonucleotide probe.

19 Claims, 5 Drawing Sheets

OSCILLATING SIGNAL AMPLIFIER FOR NUCLEIC ACID DETECTION

BACKGROUND OF THE INVENTION

Genomic DNA provides the template for the information that allows the generation of proteins which are expressed and made by an organism. These proteins are generally essential for the survival of any specific cell in an organism. Therefore, the organism requires the template to be correct and free of mistakes in order to generate a protein that is functional in a cell. If a single nucleotide of this DNA sequence is mutated (a "point mutation"), the protein may be nonfunctional. Point mutations which elicit disease states are known for many proteins. Examples include sickle cell anemia hypoxanthine phosphotransferase, and p53, a tumor suppressor gene, and several oncogenes and cancer genes.

A review by Cotton, *Biochem. J.* 263: 1 (1989), compared several methodologies for detection of point mutations with respect to the DNA type used, the DNA stage achieved, whether the mutation position was detected, the percentage of mutations detected, the time and cost requirements, and toxicity problems. Each of the methodologies examined by Cotton presents drawbacks. DNA sequencing, for example, is time consuming and expensive. Restriction enzymes do not define the mutation position and detect less than 50% of mutations. Denaturing gradient gels and SSCP, see Murakami et al., *Cancer Res.* 51:3356 (1981), do not define the mutation position and are not efficient at detecting mutations. S1 nuclease and RNAse are not efficient at detecting mutations. Finally, Carbodi-imide/ABC nuclease and carbodi-imide are efficient but generate false positives and are toxic.

Recently, point mutations have been detected with the *E. coli* repair enzyme mutY. See Hsu et ai., *Carcinogenesis* 15(8): 1657 (1994). In this method a wild type labeled probe is generated using the polymerase chain reaction (PCR) described, for example, by Saiki et al., *Nature* 324: 163 (1986). The probe then is hybridized to the unknown sample DNA wherein mutY then cleaves mismatches when an adenosine which does not form watson crick base pairing with a guanine nucleotide. The position of mutY cleavage at A/G sites can then be determined by gel electrophoresis. This methodology is limited by the use of PCR, which itself generates mutations in the amplified DNA. See Loeb et al., *Nucleic Acids & Molec. Biol.* 1: 157 (1987); Tindal et al., *Biochemistry* 27:6008 (1988); Kunkel, loc. cit. 29:8004 (1990).

Accordingly, there is a need for an accurate and efficient method of detecting point mutations using unamplified DNA source molecules. In addition, such a method would save time, require minimal equipment and is less expensive, as well decreasing the hazard of toxic chemicals. Also, methods of amplifying limiting amounts of the mutated sequences would have advantages.

For the same reasons, there is a need for accurate and inexpensive methods to detect non-mutated target polynucleotides from unamplified DNA source molecules.

Currently there are several amplification methodologies, well known to those skilled in the art, for the detection of non-mutated DNA. Among these techniques are the polymerase chain reaction (PCR), the ligase chain reaction (LCR), nucleic acid system-based amplification (NASBA), and cycling probe technology (CPT). Other amplification methods are well known to those skilled in the art.

The polymerase chain reaction described, for example, in U.S. Pat. No. 4,362,195, is the best known amplification system, but it is limited by the level of amplification ($\sim 2.2 \times 10^5$), is prone to the generation of mutations, and can generate false positives by the generation of amplified molecules contaminating the environment. Despite these limitations, PCR is widely used in the research community. It still is not approved by governmental regulators for clinical and diagnostic applications, however.

CPT technology was developed, in part to overcome the limitations of PCR. See, for example, U.S. Pat. Nos. 4,876,187 and No. 5,011,769. The CPT technology entails the use of a synthetic molecule with two non-complementary nucleic acid sequences joined by a scissile linkage. CPT technology works by observing a hybridization event with a sample nucleic acid by a single cleavage event. This technology utilizes both the enzymatic features of RNAse H and a synthetic DNA-RNA-DNA oligonucleotide. RNAse H specifically cleaves the RNA moiety of the DNA-RNA-DNA oligonucleotide only when it is perfectly hybridized to a complementary DNA target molecule. A high concentration of the DNA-RNA-DNA molecule is converted to cleaved fragments, which are assayed by gel electrophoresis. The level of cleavage indicates the amount of target molecules present in the sample.

The CPT system does not amplify the target, alleviating the accumulation of molecules that in turn become amplifiable and generate false-positives, as occurs in PCR. The CPT technology is linear, in that increasing amounts of target DNA generate linearly more cleaved DNA-RNA-DNA oligonucleotide. (PCR generates exponentially more signal in response to the presence of more target DNA, making quantitation more problematic). Additionally, CPT can amplify up to $10^6$ cleaved DNA-RNA-DNA probe molecules in about 30 minutes. CPT does not generate more of the target molecule. Therefore, it does not jeopardize the laboratory environment by the possible accumulation of synthesized target DNA molecules, which in turn generate false positive results. It also is isothermal, i.e., it does not require the use of expensive automated thermocycling equipment. Further, it has been shown to detect a single molecule. The CPT technology is limited, however, because the cleavable portion of the molecule is an RNA moiety.

SUMMARY OF THE INVENTION

It is therefore an object of the present invention to provide a method for detecting point mutations in nucleic acid sequences.

It is a further aspect of this invention to provide a simple and efficient, and sensitive method to detect point mutations in nucleic acid sequences.

It is also an object of the invention to provide a means for detecting non-mutated nucleic acid sequences.

It is yet another object of this invention target polynucleotide detection using oscillating and tagging techniques.

Still another aspect of this invention provides helix destabilizing molecule and similar molecules to enhance the hybridization of the probe to the target polynucleotides.

Yet another aspect of this invention provides for the determination of the amount of base repair enzyme activity carried out on a mutated polynucleotide sequence.

In accomplishing the foregoing objects, there is provided a method of detecting a point mutation in a target polynucleotide, comprising:

(a) hybridizing a single-stranded oligonucleotide probe, under stringent conditions, to the target polynucleotide to form a hybrid double-stranded polynucleotide such that a mismatch occurs at the site of the point mutation, wherein the probe is complementary to a non-mutated sequence of the target polynucleotide;

(b) cleaving the probe strand of the hybrid polynucleotide at the point of mismatch with a nucleic acid repair enzyme, producing oligonucleotide fragments; and (c) detecting the polynucleotide fragments.

In accomplishing the foregoing objects, there is also provided a method of detecting a sequence in a target polynucleotide, comprising the steps of:

(a) hybridizing a single-stranded oligonucleotide probe, under stringent conditions, to the target polynucleotide to form a hybrid double-stranded polynucleotide, wherein the probe contains a mismatched or repairable base sequence, such that a mismatch occurs at the site of the mismatched or repairable base sequence;

(b) cleaving the probe strand of the hybrid polynucleotide at the point of mismatch with a nucleic acid repair enzyme, (c) detecting polynucleotide fragments produced by the cleavage.

In accomplishing the foregoing objects, there is also provided a method of determining a repair index for a mismatched or damaged oligonucleotide probe, comprising (a) hybridizing a synthetic single-stranded oligonucleotide probe, under stringent conditions, to the target polynucleotide to form a hybrid double-stranded polynucleotide, wherein the probe contains a mismatched or repairable base sequence, such that a mismatch occurs at the site of the mismatched or repairable base sequence; then (b) exposing the double-stranded polynucleotide to a base-repairing enzyme, whereby less than complete repair of the mismatched or repairable base sequence is effected, leaving repaired probe and non-repaired probe;

(c) cleaving the non-repaired probe at the site with a nucleic acid repair enzyme; and (d) detecting polynucleotide fragments produced by the cleavage.

DETAILED DESCRIPTION OF PREFERRED EMBODIMENTS

Figure 1:
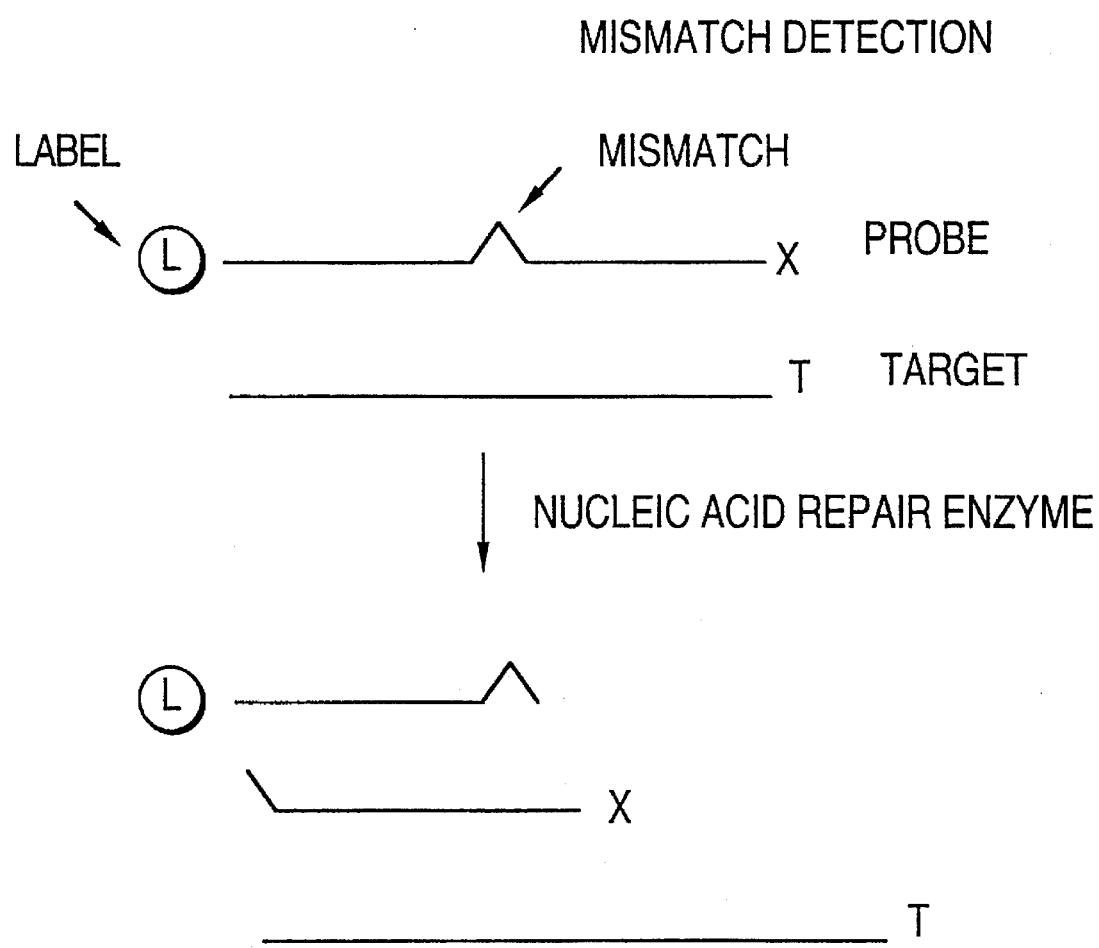
FIG. 1 is a schematic diagram showing the hybridization of probe to target polynucleotide to form a mismatch. The mismatch can be the consequence of either a wild-type probe hybridizing to a mutant target or a mutant probe hybridizing to a wild-type target. Nucleic acid repair enzyme then cleaves the probe, which dissociates from the target.

It has been discovered that the deficiencies in conventional techniques in this regard can be overcome by employing nucleic acid repair enzymes. Thus, the problems by Cotton (1989), supra, are avoided by using nucleic acid repair enzymes, in accordance with the present invention, to detect point mutations. Furthermore, nucleotide excision enzymes can be used in the present invention to detect wild-type target polynucleotide sequences and to determine the amount of base repair enzyme activity carried out on a mutated polynucleotide sequence. The present invention represents an improvement over the CPT method, because a DNA oligonucleotide suitable for the present invention can be made via more conventional chemistry (and, hence, is less expensive to synthesize) and is more stable.

Researchers have used nucleic acid repair enzymes to detect point mutations, see Hsu et al. (1994), supra, but these techniques are limited because they employ PCR to amplify the target polynucleotide. The present invention overcomes this limitation because it does not require PCR amplification. Instead, nucleic acid repair enzymes can be used to create an oscillating reaction which allows for adequate target detection using a limited amount of unamplified target. Alternatively, detection can be enhanced by using nucleic acid repair enzymes, and other enzymes, to tag the polynucleotide probe which has bound to the target polynucleotide.

Moreover, hybridization of oligonucleotide probe to polynucleotide target can be enhanced by employing helix destabilizing molecules, as described in greater detail below.

According to one embodiment of the present invention, point mutations in a target polynucleotide of biological sample can be detected, identified or localized. This embodiment does not include the use of PCR amplification of target polynucleotide, since PCR amplification introduces spurious point mutations.

This embodiment entails hybridizing a single-stranded oligonucleotideprobe to a target polynucleotide to form a hybrid, double-stranded polynucleotide. The hybridization occurs under conditions that are "stringent," which typically implicates conditions that include a 50–100mM salt solution at a temperature of 3N -20° C., where N is the number of nucleotides in the oligonucleotide probe.

As for probe design, preferably, the oligonucleotide probe is designed not to have self complementary regions, palindromic regions and the probe must also have probe specificity. The parameters for probe design can be found in Lowe et al., Nucl. Acids Res. 18:1757–1761 (1990); Rychlik et al., loc. cit. 17:8543–8551 (1989); Rychlik et al., loc. cit. 18:6409–6412 (1990), which discusses probe design as applied to PCR reactions.

Because the probe is complementary to a non-mutated sequence in the target polynucleotide, there will be a mismatch between non-mutated probe and mutated target polynucleotide. The mismatch will occur at the site of point mutation. The present invention comprehends the existence of multiple sites of mismatch on the hybrid, double-stranded polynucleotide.

The probe is cleaved at the point of mismatch with a "nucleic acid repair enzyme," which is an enzyme that will cleave, at a point of mismatch, one strand of a duplex formed by oligonucleotide probe and target polynucleotide. Examples of nucleic acid repair enzymes are mutY (Wu et al., Proc. Nat'l Acad. Sci. USA 89: 8779–83 (1992)), T/G mismatch-specific nicking enzyme from HeLa nuclear extracts (Wiebauer & Jiricny, Nature 339: 234–36 (1989); Wiebauer & Jiricny, loc. cit. 87:5842–45 (1990)), T/G mismatch-specific nicking enzyme from E. coli (Hennecke et ai., Nature 353:776–78 (1991)), human yeast all-type enzymes (Yeh et al., J. Biol. Chem. 2667: 6480–84 (1991); Chiang & Lu, Nuc. Acids Res., 19:4761–4766 (1981)).

Another example of nucleic acid repair enzyme is an enzyme system comprising a glycosylase combined with an AP cleaving enzyme, such as endonuclease or lyase. Together glycosylase and AP cleaving enzyme, such as endonuclease or lyase cleave oligonucleotide probe/target polynucleotide duplex at a point of mismatch. A glycosylase creates an abasic sugar (an AP site) at the point of mismatch, which then is cleaved by an AP cleaving enzyme, such as endonuclease or lyase. Illustrative enzymes in these categories are detailed below.

glycosylases: tag-1, alkA, ung, fpy, mutY, nth, xthA, nfo, recJ, uvtA, uvrD, mfd, mutH, mutL, mutS, uracil DNA glycosylase, hydroxymethyluracil glycosylase, 5-mC DNA glycosylase, hypoxanthine DNA glycosylase, thymine mismatch DNA glycosylase, 3-mA DNA glycosylase, hydrated thymine DNA glycosylase (endonuclease III), pyrimidine dimer glycosylase These enzymes can come from any different biological sources. For example, Friedberg et al., DNA REPAIR AND MUTAGENESIS (ASM Press 1995), lists uracil DNA glycosylases from herpes simplex virus types 1 and 2, equine herpes virus, Varicella zoster virus, Epstein Barr virus, human cytomegalovirus, Mycoplasma lactucae, E. coli, B. subtilis, M. luteus, B. steorophermaophilus, Thermothrix thirpara, S. pneumoniae, Dictyostelium discoideium, Artenia salina, S. cereVisae, Hordeum vulgare, Zea mays, Triticum vulgare, rat liver mitochondria, calf thymus, human placenta, HeLa S3 cells, and acute leukemia blast cells.

AP cleaving enzymes: E. coli exonuclease III, E. coli endonuclease IV, Saccharomyes AP endonuclease, Drosphila melanogaster AP endonuclease I and II, human AP endonuclease, human AP lyase, BAP endonuclease, APEX endonuclease, HAP1 and AP endonuclease In principle, the present invention could employ a nucleic acid repair enzyme that is thermally stable, in the sense that the enzyme would function at some elevated temperature, such as from 50° to 80° C. Additionally, the thermally stable nucleic acid repair enzyme would withstand temperatures up to 100° C. for short periods. No such thermostable nucleic acid repair enzyme has been disclosed in publication to date, however. Accordingly, it is preferable that the repair function of the enzyme employed in the invention should be effected in a temperature in the range of 40° to 70° C.

Additionally, the present embodiment can utilize a combination of nucleic acid repair enzymes. For example a nucleic acid repair enzyme can be used in combination with a AP cleaving enzyme. Advantageously, mutY is used in combination with AP cleaving enzymes, such as DNA lyase or DNA AP endonuclease. Such a system of enzymes enhances the speed at which cleavage occurs.

After cleavage by a nucleic acid repair enzyme, pursuant to the present invention, the amount of cleaved oligonucleotide probe can determined. In particular, the amount of cleaved oligonucleotide probe can be quantified to indicate the amount in a given sample of target polynucleotide containing a point mutation. The size of the cleaved oligonucleotide probe indicates the site of the mismatch in the target sample.

One method of detecting the amount of cleaved oligonucleotide probe fragments and the size of cleaved oligonucleotide probe fragments is by gel electrophoresis. Radiolabeling, fluorescent labeling or other labeling of the synthetic oligonucleotides can be used, and the processed samples then are electrophoresed on a gel, typically a 20% polyacrylamide/7M urea-1×TBE gel.

The gel then can be autoradiographed. The autoradiograph can be scanned electronically, along with control lanes containing different amounts of radiolabeled material. The density of the uncleaved and cleaved oligonucleotide can then be interpolated from electronically scanned data and controls, and the amount of cleavage quantitated. A similar process can be used for florescence using a fluorimeter. Chemiluminescence can be detected by autoradiography.

Another method for detecting probe fragments involves capillary electrophoresis. By this approach, the processed samples are electrophoresed rapidly, allowing quantitation of the amount of cleaved oligonucleotide probe and size determination. Capillary electrophoresis is described in Guttman et al., J. Chromatography 593:297–303 (1992).

Yet another method entails the use of fluorescence resonance energy transfer (FRET), which can be used by placing two fluorescent molecules at either end of the synthetic oligonucleotide. When cleavage occurs, the two fluorescent molecules are physically separated, reducing florescence. Accordingly, reduced fluorescence indicates the amount of cleaved oligonucleotide probe.

In general, hybridization of a synthetic, single-stranded oligonucleotide probe to a single-stranded target polynucleotide occurs at a temperature roughly 3° C. per nucleotide at 1M salt conditions. For a 20-mer synthetic oligonucleotide, therefore, the hybridization temperature can be predicted to be about 60° C.

In the present embodiment, hybridization can be facilitated by a helix destabilizing molecule. For instance, a helix destabilizing molecule can allow hybridization of a 20-mer synthetic oligonucleotide to target polynucleotide at 40° C.

By reducing the temperature necessary to achieve hybridization of oligonucleotide probe to target polynucleotide, helix destabilizing molecule can eliminate the need for thermostable enzymes and expensive thermocyclers.

Exemplary helix-destabilizing molecules include *I, herpes simplex virus-type I ICPS, nucleolin, and adenovirus DNA-binding protein. See Topal & Sinha, J. Biol. Chem. 258(20): 12274–79 (1983); Alberts & Frey, Nature 227: 1313–18 (1970); Hosoda & Moise, J. Biol. Chem. 253(20): 7547–55 (1978); Ghisolfi et al., loc. cit., 267(5): 2955–59 (1992); Boehmer & Lehman, J. Virol. 67(2): 711–15 (1993); Zijderveld & van der Vleit, J. Virol. 68(2): 1158–64 (1994); Monaghan et al., Nucleic Acids Research 22(5): 742–48 (1994).

When facilitated by helix-destabilizing molecule, hybridization in accordance with the present invention can be effected with long synthetic oligonucleotides, without the use of thermostable enzymes or expensive thermocyclers. A "long" oligonucleotide in this context is greater than 25 nucleotides but preferably not greater than 100 nucleotides. Use of such long oligonucleotides affords the advantage of hybridizing to the target polynucleotide with increased specificity.

The presence of a helix-destabilizing molecule thus allows for the use of long synthetic oligonucleotides, without thermostable enzymes or expensive thermocyclers. The helix-destabilizing molecule allows for the dispensation of thermostable enzymes because it lowers the temperature necessary for hybridization. In some instances, however, the helix-destabilizing molecule will not lower the temperature sufficiently to allow for the dispensation of thermal stable enzymes. In these instances, the present invention could, in principle employ a helix-destabilizing molecule that is thermally stable, in the sense that the enzyme would function at some elevated temperature, such as from 50° to 80° C. Additionally, the thermally stable enzyme would withstand temperatures up to 100° C. for short periods. No such thermostable helix-destabilizing molecule has been disclosed in publication to date, however. Accordingly, it is preferable that the destabilizing function of the enzyme employed in the invention should be effected in a temperature in the range of 40° to 70° C.

Detecting of point mutations, in accordance with the present embodiment, is useful in detecting diseases resulting from inherited genetic mutations. There are many well known examples of such diseases, including sickle cell anemia, and diseases resulting from the mutation of p53 cancer tumor suppressor gene, hypoxanthine phosphotransferase, and oncogenes. In each of these cases, the gene contains a detectable nucleotide or nucleotides that have been mutated to a different base. These point mutations cause the disease state in the individual.

OSCILLATION REACTION

In another embodiment of this invention, an oscillation reaction is created whereby the nucleic acid repair enzyme cleaves the oligonucleotide probe, and the shortened, cleaved oligonucleotide fragments dissociate from the target polynucleotide at a predetermined temperature. That is, The oligonucleotide probe is designed so that, at the predetermined temperature, the oligonucleotide fragments dissociate from the target polynucleotide after cleavage by nucleic acid repair enzyme. A cycle or oscillation reaction then occurs because the target polynucleotide hybridizes to another oligonucleotide probe, and the cleavage process is repeated.

As a consequence, a small number of target polynucleotides can be detected in a sample, since a single target polynucleotide catalyses the formation of a large number of oligonucleotide probe cleavage fragments. The oscillation reaction enables the detection of as little as one molecule of target polynucleotide in a sample. The oscillation reaction can detect from 10–100 target polynucleotide molecules in a sample. Theoretically, the oscillation reaction may detect as little as one target polynucleotide molecule in a sample.

To accommodate the oscillation reaction, a high concentration of oligonucleotide probe is utilized. In this regard, a suitable radiolabeled probe concentration is from 0.01 to 10 pmol. Other concentrations can be used depending on the desired length of autoradiograph exposure times.

One of skill in the art can refer to Duck et al., *BioTechniques* 9(2): 142 (1990), which refers to CPT a similar but less advantageous technique for amplifying probe.

Preferably, the oscillating reaction is performed at a isothermal temperature of 3N—20° C., here N is the length of the probe in base pairs. Within this working range the optimal temperature is determined empirically. Preferably, the reaction is performed with 0.01 to 10 pmol of labeled probe, in the presence of either synthetic target sequence or DNA purified from a sample source. This target DNA will ranges from 1 to $10^{12}$ molecules.

To reduce the double stranded nature of the target DNA the DNA can be partially degraded with DNAse I to form shorter DNA fragments. The reaction can also be performed in the presence of 10 to 100 pmol of a helix destabilizing molecule in the presence of 5 to 10mM $Mg^{-2}$. With the helix destabilizing molecule the operating temperature will need to be empirically determined.

A typical reaction is performed in a buffer composed of 20 mM Tris-HCL, pH 7.6, 80 mM NaCl, 1 mM dithioerythritol, 1 mM EDTA, pH 8.0, with 5 to 50 units of mutY enzyme. The reaction is allowed to proceed for 20 to 60 minutes, a loading dye of 98% formamide, 10 mM EDTA, pH 8.0, 0.025% xylene Cyanol FF, 0.025% Bromophenol blue is added to stop the reaction. The sample is then loaded onto a 20% acrylamide/7M urea 1×TBE gel and electrophoresed about 10 to 15 cm at 200 to 500 V. The gel is then autoradiographed for 1 minute to 5 days, dependent on the amount and specific activity of the probe, which is prepared by standard kinasing reaction conditions for T4 polynucleotide kinase.

Labeled Tail

In another embodiment of the present invention, the detection of cleaved oligonucleotide fragment is enhanced by the addition of a labeled tail. To add a labeled tail to a cleaved oligonucleotide fragment, an oligonucleotide probe can be synthesized so that it forms a mismatch when hybridized to target polynucleotide. The oligonucleotide probe can contain a protected 3' group, preventing a polymerase from extending from the probe sequence. The probe then can be cleaved by a nucleic acid repair enzyme.

Figure 2:
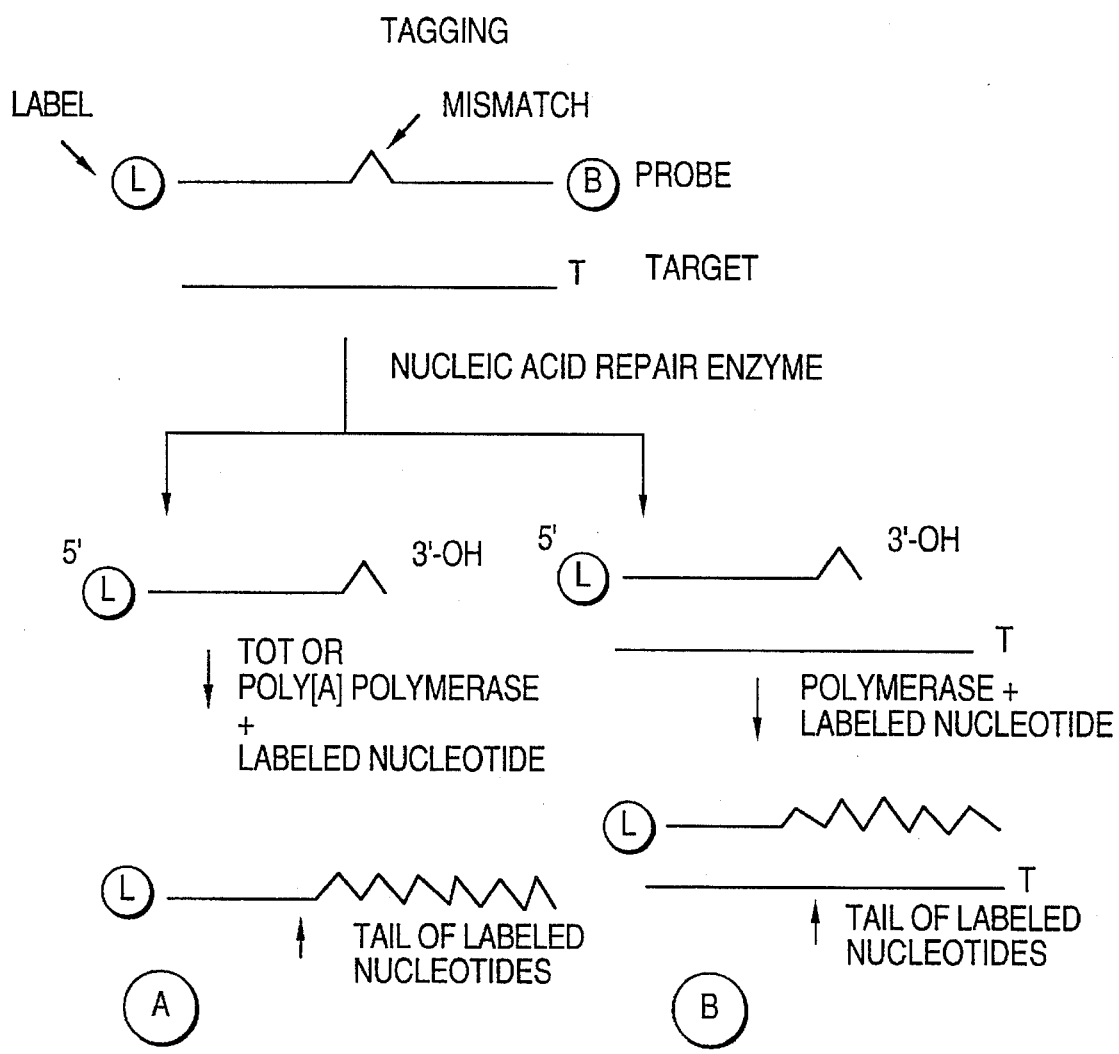
FIG. 2 is a schematic drawing showing the tail labeling of cleaved probe. Probe is cleaved at the site of mismatch. If the probe is designed to dissociate, as shown in part A, it can, after dissociation, be tagged with a labeled nucleotide tail. If the probe is designed to remain hybridized to target after cleavage, as shown in part B, then it can also be tagged with a labeled nucleotide tail.

In one aspect of the present embodiment, represented by side B of FIG. 2, the 5' region of the probe can be designed so that it is long enough to remain bound to the target sequence when the mismatch is cleaved. The 3' region of the probe can be designed so that it is short enough so that upon cleavage it dissociate from the target polynucleotide.

The 5' region of the probe that upon cleavage has remained bound to the target polynucleotide now can form a template for DNA polymerase with appropriate dNTPs, as shown in side B of FIG. 2.

If the nucleotides used in this embodiment are labeled with a radionucleotide or with some other marker, such as a fluorescent label, then the amount of cleavage can be assayed, using these labeled nucleotides as the signal.

In another aspect of the present embodiment, the 5' region is so designed that it dissociates from the target polynucleotide when the mismatch is cleaved, as shown in side A of FIG. 2. The 5' cleavage fragment then can be extended with polyA polymerase or terminal deoxynucleotidyl transferase (TdT), as shown in side A of FIG. 2, and detected.

For example, if the tails consist of polymers of adenosines, the tails will hybridize to polymers of oligonucleotide composed of thymines. If the nucleotides used in this polyA polymerase or TdT reaction are labeled with a radionucleotide or with some other marker, such as a fluorescent label, then the amount of cleavage can be assayed, using these labeled nucleotides as the signal.

Additionally, the oligonucleotide probe described in the previous two aspects of the present embodiment can have another feature, a ligand type molecule at the 5' end of the probe oligonucleotide. The ligand can serve to label the probe. The ligand can be a biotin group, or a group extendable with poly (ADP) ribose polymerase. Additionally, the ligand can be DNP (dinitrophenol) or cholesterol moieties.

By attaching a ligand molecule to the 5' end of the probe oligonucleotide, molecules that bind to the ligands, such as antibodies can be used to affinity purify the newly formed tails. For example, after cleavage the probes with a biotin ligand can be passed over an avidin or streptavidin column. The probes with a poly(ADP)ribose ligand can be passed over a antipoly(ADP)ribose column. The DNP and cholesterol moieties can be passed over column with antibody against DNP and cholesterol, respectively. Affinity purification techniques, including affinity chromatography are well known to those skilled in the art.

Detecting Known Sequences

Yet another embodiment of this invention provides for detecting, identifying, measuring, or localizing, inter alia, known sequences in a target polynucleotide in a biological sample. This aspect of the invention includes hybridizing a single-stranded oligonucleotide probe to a target polynucleotide to form a hybrid double-stranded polynucleotide. In this embodiment, the probe is designed so that it includes a mismatched or repairable base sequence.

Because the probe so designed is not complementary to the target polynucleotide, there is a mismatch between the probe containing a synthesized mutation or mismatch site and the wild-type target polynucleotide. The mismatch occurs at the site of a mismatched or repairable base sequence.

The probe is cleaved at the point of mismatch with a nucleic acid repair enzyme as mentioned above. The cleaved polynucleotide fragments are then detected as mentioned above.

An example of the present embodiment is as follows. The probe oligonucleotide can be synthesized so that it is complementary to the target polynucleotide sequence except at a single nucleotide, which is chosen to be near the middle of the probe. The wild-type probe contains a cytosine base in the middle of the probe that correctly hybridizes to a guanosine base on a wild-type target polynucleotide sequence. The mismatched probe can be designed by synthesizing an oligonucleotide probe wherein the cytosine base is replaced by an adenine base. The adenine base of the probe oligonucleotide mismatches to a guanosine base in the target molecule. But the rest of the strands of the probe and target are complementary. When treated with mutY, the probe are cleaved if it has hybridized to a non-mutated wild-type target polynucleotide.

If, however, the target polynucleotide contains a point mutation, so that the aforementioned target guanosine is in fact a thymine, the probe containing a mutation will not be cleaved. This is true because a mismatch will not have occurred, the probe adenine being complementary to the target thymine.

Another aspect of the present embodiment includes two probes, used independently, which contain mismatches at slightly different sites. Cleavage occurring for both probes in separate reactions confirms the presence of the target polynucleotide.

The present embodiment can employ helix destabilizing molecules, as discussed above. Additionally, this embodiment can be performed using the oscillating and tailing methods already described.

The present embodiment is useful in DNA diagnostics and DNA profiling.

Detecting the Repair Index in a Sample

Yet another embodiment of the present invention comprehends detecting the repair index of a mismatched or damaged oligonucleotide probe. The "repair index" in this regard is defined as the ratio of the amount of cleavage in a sample mixed with base-repairing enzyme (shown in the right side of FIG. 3) to the amount of cleavage in a sample of control, which contains no base-repairing enzymes (control shown in FIG. 3 on left side).

The repair index indicates the extent to which base-repairing enzymes have repaired a sample of mismatched or damaged oligonucleotide probes. A "base-repairing enzyme" is one that effects repair of a mismatched probe sequence that has hybridized to a target polynucleotide. The base-repairing enzyme replaces the mismatched base with a base that is complementary to the target polynucleotide. Examples of base-repairing enzymes are *E. coli* DNA purine transferase (E.C. 2.6.99.1), human $O^6$-methylguanine-DNA methyltransferase (Koike et al, *J. Biol. Chem.* 265: 14754) and *E. coli* DNA photolyase (EMBL Data Library Accession Number S32737).

Figure 3:
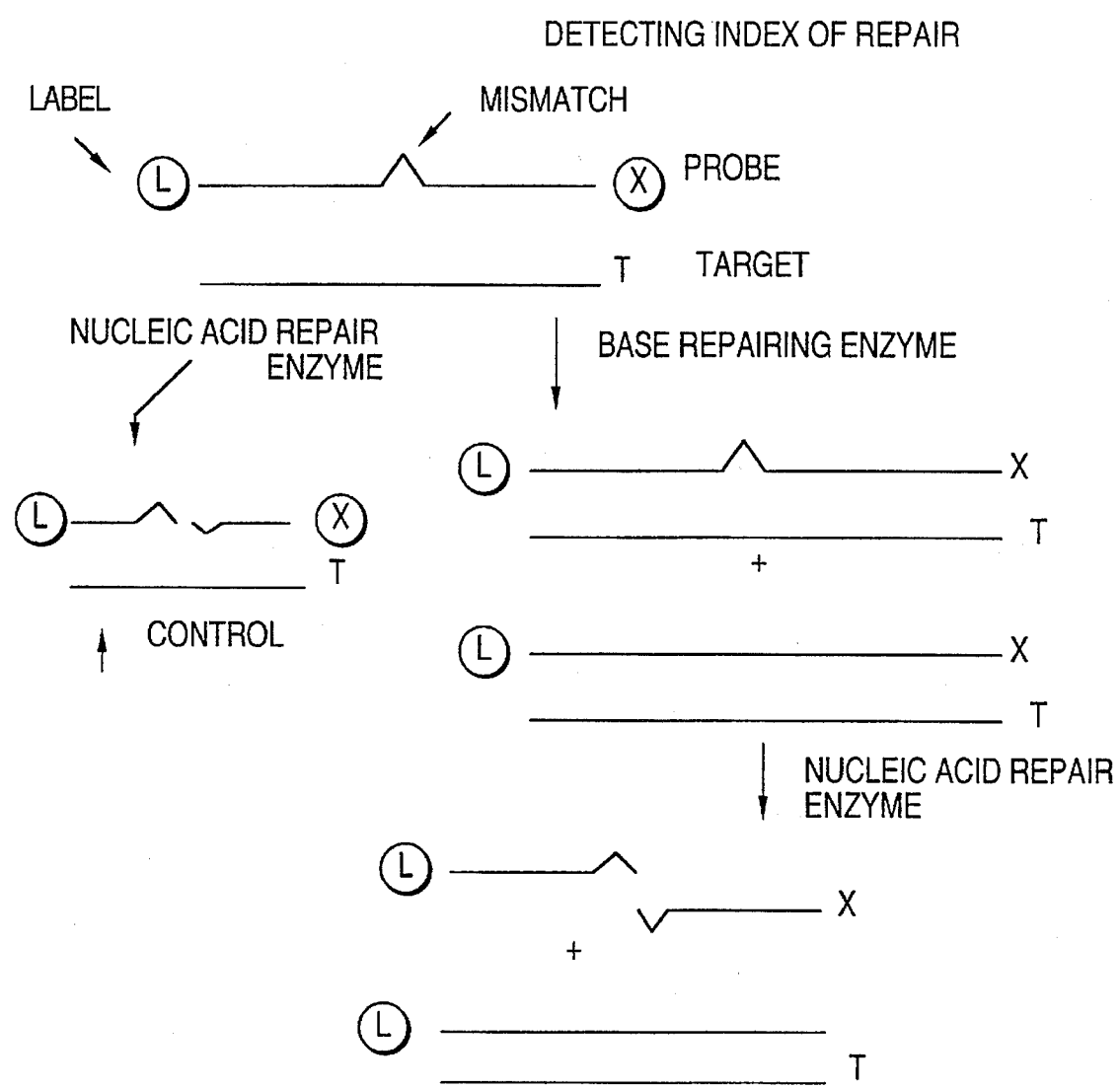
FIG. 3 is a schematic drawing showing the detection of the index of repair of a mutated or damaged probe. Probe is hybridized to target and then base-repairing enzyme is added. Next, nucleic acid repair enzyme is added and cleaves those probes which have not been repaired. A control group is shown on the left side of the figure.
Figure 4:
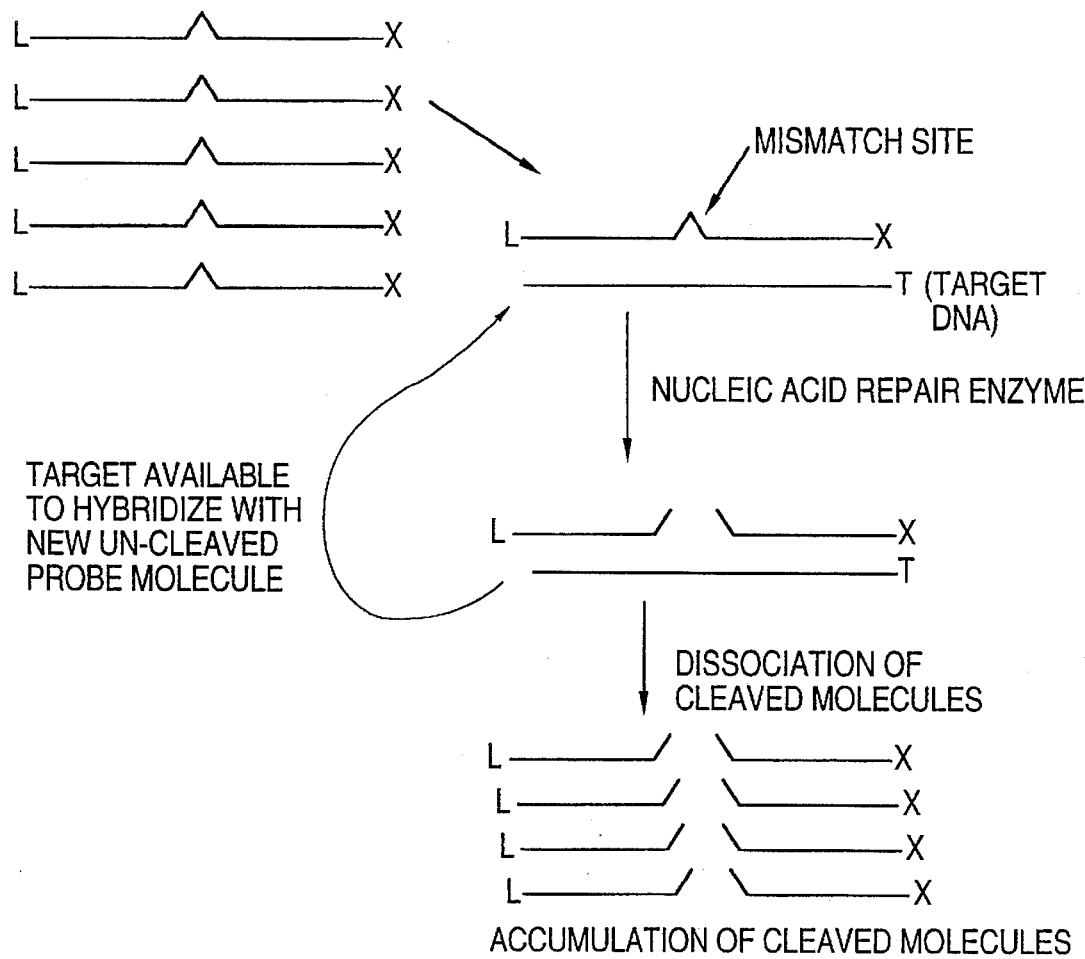
FIG. 4 is a schematic drawing showing the oscillating reaction. An excess of mismatch probe hybridize to available target molecules in the reaction mixture, wherein a Nucleic Acid Repair Enzyme cleaves at the mismatch site. The probe molecule is designed so that the shorter cleaved molecules dissociate from the target molecule. The target then hybridizes to a new intact probe molecule, generating the oscillating reaction. The accumulation of cleaved molecules is linear with the amount of target molecules available.

The embodiment depicted in FIG. 3 involves hybridizing a single-stranded oligonucleotide probe to a target polynucleotide to form a hybrid double-stranded polynucleotide. The probe is designed so that it includes a mismatched or a repairable base sequence. Such a probe can be designed according to the methods described above.

Because probe so designed will not be complementary to the target polynucleotide, there will be a mismatch between the mutated probe and the wild-type target polynucleotide. The mismatch will occur at the site of the mismatched or repairable base sequence.

Next, the hybrid double-stranded polynucleotide will be exposed to a base-repairing enzyme, which is defined above. The base-repairing enzyme will repair a certain amount of the mismatched or repairable base sequences, depending on the type of base-repairing enzymes employed.

The hybrid double-stranded polynucleotide then will be exposed to a nucleic acid repair enzyme, which cleaves non-repaired probe at the point of mismatch. The cleaved nucleotide fragments can then be detected by the methods described above.

To obtain the repair index, as defined above, the amount of cleavage in a sample mixed with base-repairing enzyme is compared to the amount of cleavage in a sample of unrepaired control.

Determining the repair index is useful in determining the potency of cancer therapeutic agents on an individual. For example, an oligonucleotide is synthesized with a base that has been modified to contain a base adduct. Several base adducts are known to be the result of certain chemotherapuetic drugs. See Friedman et al., supra, table 5-3. Base adducts cause a significant distortion of the DNA helix and are both repairable by base repair enzymes and cleaved by nucleic acid repair enzymes.

Next, the probe is hybridized with target polynucleotide in a medium containing the base-repairing enzymes of a particular individual, and then the duplex is exposed to nucleic acid repair enzyme. Accordingly, the index of repair indicates the extent to which the individual would repair mutations that would be induced by a particular cancer therapeutic agent.

The present embodiment can employ helix destabilizing molecules as described above. Additionally, this embodiment of the invention can be preformed using the oscillating and tailing methods described above.

The following examples merely illustrate the invention and, as such, are not to be considered as limiting the invention set forth in the claims.

EXAMPLE 1

Detection of Point Mutation Using the Oscillation Reaction

The enzyme mutY was purified by the method of Wu et al., Proc. Nat'l Acad. Sci. USA 89:8779–83 (1992), to a concentration of about 50 units·$\mu l^{-1}$ from an overexpressed E. coli clone. (One unit is defined as the conversion of 1 fmol A/G mismatch synthetic oligonucleotide converted to nicked substrate per minute.) Two synthetic oligodeoxyribonucleotides were synthesized by standard phosphoramidite chemistries with the following sequences:

| Oligonucleotide #1: | 5'-CCGAGGAATTAGCCTTCTG-3' |
| Oligonucleotide #2: | 5'-GCAGAAGGCGAATTCCTCG-3' |

The oligonucleotides were purified on 20% acrylamide/7M Urea 1XTBE gels to about 95% homogeneity. The fragment was detected by autoradiography and a band cut from the gel. It was eluted from the gel slice by electrophoresis onto NA-45 paper (Schleicher & Schuler, Inc) by band interception, followed by elution from the paper by heating at 65° C. for 5 minutes in 2M TEAA (triethylammonium acetate). The sample was dried in a vacuum centrifuge until all solvent was removed.

Oligonucleotide #1 (Oligo 1) was radiolabeled to high specific activity with about 60 pmols (0.1 mCi; 6000 Ci·mMol$^{-1}$) 32P-g-ATP and 100 units of T4 polynucleotide kinase at 37° C. for 1 hour. The radiolabeled fragment was further gel purified, as described above.

Oligonucleotide #2 (Oligo 2) was diluted from 1 pmol·$\mu l^{-1}$ to $10^{-9}$ pmol·$\mu l^{-1}$ in sterile deionized water.

A typical reaction mix was set up that contained about 0.2 pmol of radiolabeled oligo 1, mutY buffer (20 mM Tris-HCl, pH 7.6, 80 mM NaCl, 1 mM dithioerythritol, 1 mM EDTA, pH 8.0, 3% glycerol; final concentration), 50 units of mutY enzyme, some reactions contained a dilution of Oligo 2 from 1 to $10^{-9}$ pmol. The final volume was 10 $\mu l$. The reaction proceeded at 37° C. for 60 minutes. The reaction was stopped by the addition of 1 $\mu l$ of loading buffer (98% Formamide, 10 mM EDTA, pH 8.0, 0.025% Xylene Cyanol FF, 0.025% Bromophenol Blue). The reaction was electrophoresed on a 20% acrylamide/7M Urea 1×TBE gel, then autoradiographed. Lane 1 contains no target molecule. Lanes 2 to 11 contain $10^0$, $10^{-1}$, $10^{-2}$, $10^{-3}$, $10^{-4}$, $10^{-5}$, $10^{-6}$, $10^{-7}$, $10^{-8}$, $10^{-9}$ pmol of target. The cleavage from the reaction was detected by the generation of a smaller cleaved synthetic oligonucleotide fragment found in lanes 2 to 4. The truncated shorter molecule was due to cleavage at the A/G mismatch by the mutY enzyme.

EXAMPLE 2

Detecting Mismatches Using the Oscillation Reaction and Helix Destabilizing Molecule The nucleic acid repair enzyme mutY and the helix destabilization enzyme *I were used along with three synthetic oligonucleotides having the sequences:

| (1) 5'-CCGAGGAATTAGCCTTCTG-3' | Probe Mismatch |
| (2) 5'-CCGAGGAATTCGCCTTCTG-3' | Probe Wild-Type |
| (3) 5'-GCAGAAGGCGAATTCCTCG-3' | Target |

The three DNA synthetic oligonucleotides were used as is or were radiolabeled with $^{32}$P-$\gamma$-ATP via T4 polynucleotide kinase.

Reactions were set up as indicated below with combinations of radiolabeled or cold oligonucleotides 1, 2 and 3, with or without mutY and or *I. Lanes 1 to 20 contained radiolabeled oligonucleotide 1. Lanes 3 and 4 contained radiolabeled oligonucleotide 2. Lanes 5 to 7 contained radiolabeled oligonucleotide 3. Lane 6 contained 10 pmols of cold oligonucleotide 1. Lane 7 contained 10 pmols of cold oligonucleotide 2. Lanes 2, 4, 9 and 16 contained 10 pmols of cold oligonucleotide 3. Lanes 10 and 17, Lanes 11 and 18, Lanes 12 and 19, Lanes 13 and 20, Lane 14 contained 1, 0.1, 0.01, 0.001, 0.0001, respectively of cold oligonucleotide 3. Lanes 2, 4,6 to 20 contained mutY enzyme. Lanes 15 to 20 contained *I. The reactions were setup with standard mutY reaction buffer and allowed to proceed for 1 hour at 37° C. The reactions were stopped, loading dye was added, and the material was run on a 20% acrylamide/7M Urea gel (1XTBE).

This experiment showed that the wild-type probe showed no cleavage. The probe with a mismatch showed cleavage. The presence of *I enhanced the rate of cleavage.

Only lanes 2, 9–14 and 16–20 showed any level of cleaved molecules dependent on target concentration. This showed that only the mismatch probe cleaves when hybridized to its target sequence. The target was not cleaved in this reaction with either the mismatch (lane 6) or wild-type probe (lane 7). Further, the wild-type probe was not cleaved with mutY (lane 4).

EXAMPLE 3

Oscillating Reaction

In a hybridization reaction, a synthetic oligonucleotide of length N nucleotides has a temperature of hybridization (melting temperature or Im, in ° C.) equal to 3N. For example, a synthetic oligonucleotide of 20 nucleotides has a temperature of hybridization of about 60° C. A shorter synthetic oligonucleotide of 10 nucleotides has a temperature of hybridization of about 30° C. At a set temperature, such as 45° C., the long 20-mer synthetic oligonucleotide hybridizes but the shorter 10-mer synthetic oligonucleotide does not.

The longer synthetic oligonucleotide hybridizes to a target sequence, then when it is cleaved at a specific place where a mismatch occurs two or more shorter synthetic oligonucleotides are be generated, which have lower thermodynamic stability. These shortened cleaved oligonucleotides dissociate from the target sequence, making it available for another hybridization event with the longer synthetic oligonucleotide. By using a high concentration of the longer original synthetic oligonucleotide probe sequence (mutation probe) the hybridization kinetics favors better, faster hybridization. Further, this allows the detection of a hybridization event by the accumulation of the shortened oligonucleotide fragments.

EXAMPLE 4

Helix Destabilization

A helix destabilizing molecule can also be added to the system of Example 3. In Example 3 the operating temperature is 45° C. and is kept at that temperature for this example. In a mode where a helix destabilizing molecule functions to reduce the hybridization temperature, the longer 20-mer synthetic oligonucleotide hybridizes not at 60° C., but rather at a lower temperature, for example, 48° C. At this temperature the hybridization temperature and the operating temperature are closer. This allows in one scenario the reduction of the operating temperature to a lower temperature, perhaps 37° C. Under this situation, mesophilic enzymes (those that function around 37° C.) can be used in the reaction. The practice of this example at such a temperature is advantageous in that it does not require thermophilic enzymes (those that function at high temperature extremes, e.g. 60°–70° C., and can withstand near boiling temperatures).

EXAMPLE 5

Oligonucleotide Directed In Vitro Mutagenesis

For modifying and generating new genetic sequences, in vitro mutagenesis is used. The earliest method of in vitro mutagenesis is that of M. Smith and S. Gilliam (1981), in 3 GENETIC ENGINEERING 1 (J. K. Setlow & A. Hollaender, eds.).

The nucleic acid repair enzymes can be used for oligonucleotide directed in vitro mutagenesis. For this example, the mutY is used as the example nucleic acid repair enzyme, however, other enzymes can also be used.

Figure 5:
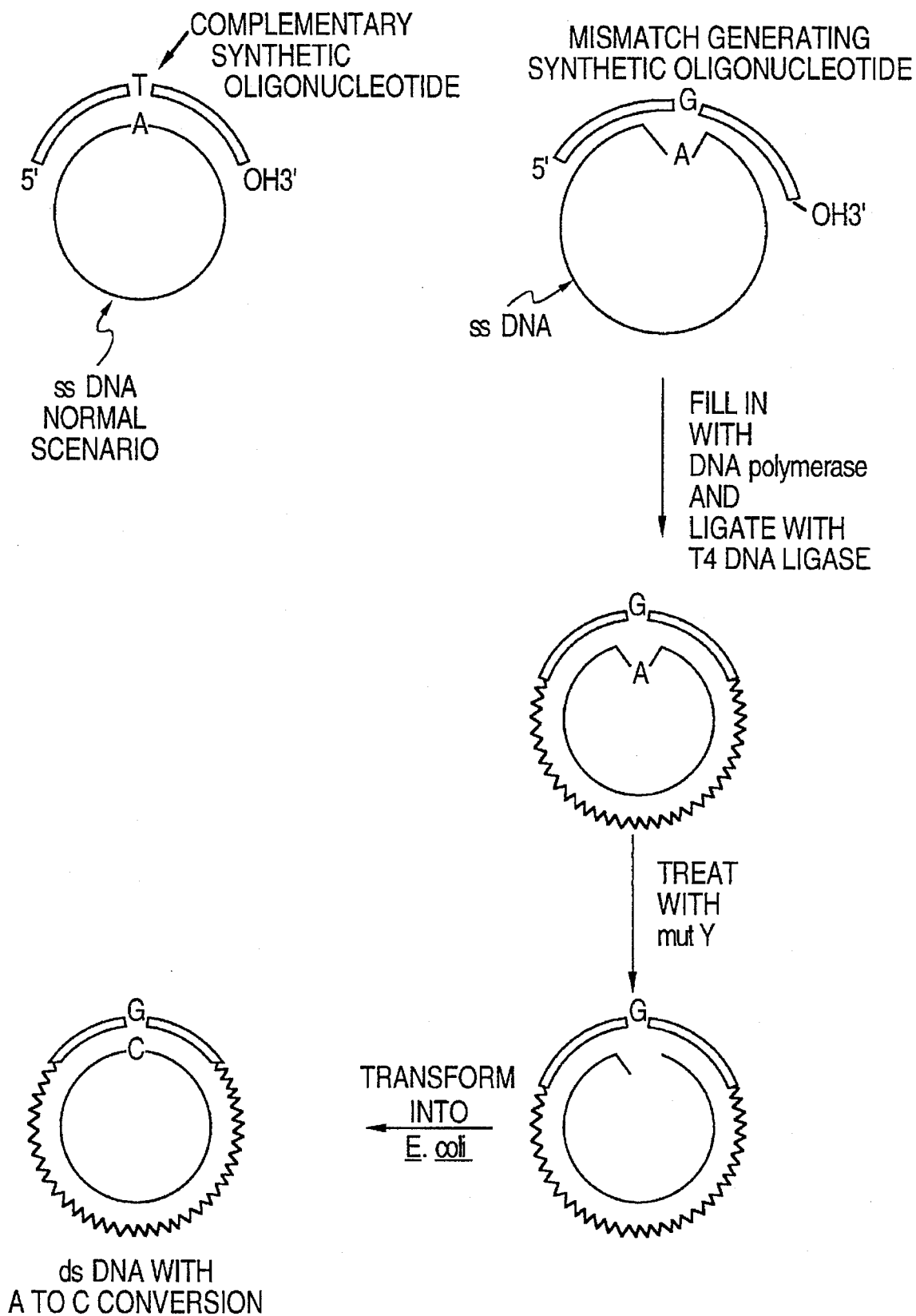
FIG. 5 is a schematic drawing showing an oligonucleotide directed in vitro mutagenesis reaction. A probe is hybridized to single stranded DNA (ssDNA) generating a mismatch in the ssDNA. A new strand of DNA is synthesized in vitro with DNA polymerase and ligase, generating a double stranded DNA (dsDNA) molecule. This dsDNA molecule is treated with mutY, cleaving and removing the mismatched base. The cleaved dsDNA molecule is transformed into *E. coli*, and the replicated dsDNA molecule then has a different base at the site of the mismatch.

Single stranded DNA containing the cloned gene sequence to be modified can be generated by the method of Zinder & Boeke, Gene 19: 1–10 (1982), using the M13 bacteriophage system. A synthetic oligonucleotide is designed, which is complementary to the region to be modified with a Guanine mismatch at a position where the adenine is to be changed to a Cytosine (FIG. 5). The oligonucleotide is hybridized to the single stranded DNA, treated with T4 DNA polymerase and T4 DNA ligase by methods used by Smith (1981). The newly synthesized double stranded molecule with a single mismatch is then treated with 50 units of mutY in mutY buffer (20 mM Tris-HCl, pH 7.6, 80 mM NaCl, 1 mM dithioerythritol, 1 mM EDTA, pH 8.0) for one hour at 37° C. The material that is cleaved at the mismatch cite is transformed into *E. coli* using methods well known to those skilled in the art. The transformants then are enriched for sequences containing the conversion of the adenine to the cytosine base pair.

It will be apparent to those skilled in the art that various modifications and variations can be made to the processes of this invention. Thus, it is intended that the present invention covers the modifications and variations provided they fall within the scope of the appended claims and their equivalents.

All of the aforementioned documents are expressly incorporated herein by reference in their entirety.

What is claimed is:

1. A method of detecting a point mutation in a target polynucleotide, consisting essentially of:
   (a) hybridizing a single-stranded oligonucleotide probe, under stringent conditions, to said target polynucleotide to form a hybrid double-stranded polynucleotide such that a mismatch occurs at the site of said point mutation, wherein said probe is complementary to a non-mutated sequence of said target polynucleotide;
   (b) cleaving said probe strand of said hybrid polynucleotide at said point of mismatch with a nucleic acid repair enzyme, producing oligonucleotide fragments, wherein said oligonucleotide probe is designed such that said cleavage results in dissociation of said oligonucleotide fragments from said target polynucleotide spontaneously at a predetermined temperature;
   (c) repeating steps (a) and (b);
   (d) detecting said polynucleotide oligonucleotide fragments; and thereby
   (e) detecting said point mutation.

2. A method according to claim 1, wherein (i) the 3' end of said oligonucleotide probe is blocked, whereby chain extension is prevented; (ii) said oligonucleotide probe is designed such that cleavage thereof results in (a) a 5' probe sequence that remains bound to said target and (b) a blocked 3' probe sequence that dissociates from said target polynucleotide; and (iii) said method further comprises, before step (c), the step of adding a labeled nucleotide tail to said 5' probe sequence which allows detection of said target polynucleotide.

3. A method according to claim 1, wherein (i) the 3' end of said oligonucleotide probe is blocked, whereby chain extension is prevented; (ii) said oligonucleotide probe is designed such that cleavage thereof results in a 5' probe sequence and a blocked 3' probe sequence dissociating from said target polynucleotide; and (iii) before step (c), the step of adding a labeled nucleotide tail to said 5' probe sequence which allows detection of said target polynucleotide.

4. A method according to claim 1, wherein said nucleic acid repair enzyme is an enzyme from the group consisting of mutY, T/G mismatch-specific nicking enzyme, and human yeast all-type enzyme.

5. A method according to claim 4, wherein said nucleic acid repair enzyme is combined with DNA lyase or DNA endonuclease.

6. A method according to claim 1, wherein a helix destabilizing molecule is present in step (a) to reduce hybridization temperature, whereby said hybridizing is facilitated.

7. A method of detecting a sequence in a target polynucleotide, comprising the steps of:
   (a) hybridizing a single-stranded oligonucleotide probe, under stringent conditions, to said target polynucleotide to form a hybrid double-stranded polynucleotide, wherein said probe contains a mismatched or repairable base sequence, such that a mismatch occurs at the site of said mismatched or repairable base sequence;
   (b) cleaving said probe strand of said hybrid polynucleotide at said point of mismatch with a nucleic acid repair enzyme, producing oligonucleotide fragments, wherein said oligonucleotide probe is designed such that said cleavage results in dissociation of said oligonucleotide fragments from said target polynucleotide spontaneously at a predetermined temperature;
   (c) repeating steps (a) and (b);
   (d) detecting polynucleotide said oligonucleotide fragments produced by said cleavage; and thereby
   (e) detecting said sequence in said target polynucleotide.

8. A method according to claim 7, wherein (i) the 3' end of said oligonucleotide probe is blocked, whereby chain extension is prevented; and (ii) said oligonucleotide probe is designed such that cleavage thereof results in (1) a 5' probe sequence that remains bound to said target and (2) a blocked 3' probe sequence that dissociates from said target polynucleotide; and wherein said method further comprises, before step (c), adding a labeled nucleotide tail to said 5' probe sequence which allows detection of said target polynucleotide.

9. A method according to claim 7, wherein (i) the 3' end of said oligonucleotide probe is blocked, whereby chain extension is prevented; (ii) said oligonucleotide probe is designed such that cleavage thereof results in a 5' probe sequence and a blocked 3' probe sequence dissociating from said target polynucleotide; and (iii) before step (c), the step of adding a labeled nucleotide tail to said 5' probe sequence which allows detection of said target polynucleotide.

10. A method according to claim 7, wherein said nucleic acid repair enzyme is an enzyme from the group consisting of mutY, T/G mismatch-specific nicking enzyme, and human yeast all-type enzyme.

11. A method according to claim 10, wherein said nucleic acid repair enzyme is combined with DNA lyase or DNA endonuclease.

12. A method according to claim 7, wherein a helix destabilizing molecule is present in step (a) to reduce hybridization temperature, whereby said hybridizing is facilitated.

13. A method of determining a repair index for a mismatched or damaged oligonucleotide probe, comprising
    (a) hybridizing a synthetic single-stranded oligonucleotide probe, under stringent conditions, to said target polynucleotide to form a hybrid double-stranded polynucleotide, wherein said probe contains a mismatched or repairable base sequence, such that a mismatch occurs at the site of said mismatched or repairable base sequence; then
    (b) exposing said double-stranded polynucleotide to a base-repairing enzyme, whereby less than complete repair of said mismatched or repairable base sequence is effected, leaving repaired probe and non-repaired probe;
    (c) cleaving said non-repaired probe at said site with a nucleic acid repair enzyme;
    (d) detecting polynucleotide fragments produced by said cleavage; and thereby
    (e) determining said repair index.

14. A method according to claim 13, wherein said oligonucleotide probe is designed such that cleavage in step (b) results in dissociation of said oligonucleotide fragments from said target polynucleotide spontaneously at a predetermined temperature, and wherein step (b) is carried out at said predetermined temperature, such that said dissociation occurs and steps (a) and (b) repeat.

15. A method according to claim 13, wherein (i) the 3' end of said oligonucleotide probe is blocked, whereby chain extension is prevented, and (ii) said oligonucleotide probe is designed such that cleavage thereof results in (1) a 5' probe sequence that remains bound to said target and (2) a blocked 3' probe sequence that dissociates from said target polynucleotide; and wherein said method further comprises, before step (c), adding a labeled nucleotide tail to the free 3' end of said 5' sequence which allows detection of said target polynucleotide.

16. A method according to claim 13, wherein (i) the 3' end of said oligonucleotide probe is blocked, whereby chain extension is prevented; (ii) said oligonucleotide probe is designed such that cleavage thereof results in a 5' probe sequence and a blocked 3' probe sequence dissociating from said target polynucleotide; and (iii) before step (c), the step of adding a labeled nucleotide tail to said 5' probe sequence which allows detection of said target polynucleotide.

17. A method according to claim 13, wherein said nucleic acid repair enzyme is an enzyme from the group consisting of mutY, T/G mismatch-specific nicking enzyme, and human yeast all-type enzyme.

18. A method according to claim 17, wherein said nucleic acid repair enzyme is combined with DNA lyase or DNA endonuclease.

19. A method according to claim 13, wherein a helix destabilizing molecule is present in step (a) to reduce hybridization temperature, whereby said hybridizing is facilitated.

* * * * *